US008088734B2

(12) United States Patent
Mehta et al.

(10) Patent No.: US 8,088,734 B2
(45) Date of Patent: Jan. 3, 2012

(54) ORAL DELIVERY OF PEPTIDES

(75) Inventors: Nozer M. Mehta, Randolph, NJ (US); William Stern, Tenafly, NJ (US); James P. Gilligan, Union, NJ (US)

(73) Assignee: Unigene Laboratories Inc., Fairfield, NJ (US)

( * ) Notice: Subject to any disclaimer, the term of this patent is extended or adjusted under 35 U.S.C. 154(b) by 0 days.

(21) Appl. No.: 10/761,481

(22) Filed: Jan. 20, 2004

(65) Prior Publication Data

US 2004/0197323 A1    Oct. 7, 2004

Related U.S. Application Data

(60) Provisional application No. 60/441,856, filed on Jan. 21, 2003.

(51) Int. Cl.
*A61K 38/26* (2006.01)
*A61K 38/28* (2006.01)
*A61K 38/29* (2006.01)

(52) U.S. Cl. ............ 514/11.8; 514/5.9; 514/11.7
(58) Field of Classification Search .......... None
See application file for complete search history.

(56) References Cited

U.S. PATENT DOCUMENTS

| | | | | |
|---|---|---|---|---|
| 3,853,834 A * | 12/1974 | Shields | | 530/313 |
| 4,086,196 A | 4/1978 | Tregear | | 260/112.5 |
| 4,604,376 A | 8/1986 | Teng | | 514/3 |
| 4,708,934 A | 11/1987 | Gilligan et al. | | 435/68 |
| 4,771,124 A | 9/1988 | Rosenblatt et al. | | 530/324 |
| 4,804,742 A * | 2/1989 | Neiss et al. | | 530/307 |
| 4,994,439 A | 2/1991 | Longenecker et al. | | 514/3 |
| 5,100,662 A * | 3/1992 | Bolcsak et al. | | 424/450 |
| 5,120,712 A | 6/1992 | Habener | | 514/12 |
| 5,122,376 A | 6/1992 | Aliverti et al. | | 424/405 |
| 5,157,021 A | 10/1992 | Balschmidt et al. | | 514/3 |
| 5,206,219 A | 4/1993 | Desai | | 514/3 |
| 5,288,497 A | 2/1994 | Stanley et al. | | 424/440 |
| 5,310,727 A | 5/1994 | Lattanzi et al. | | 514/12 |
| 5,312,899 A | 5/1994 | Schiller | | 514/18 |
| 5,350,741 A | 9/1994 | Takada | | 514/3 |
| 5,447,729 A | 9/1995 | Belenduik et al. | | 424/490 |
| 5,472,710 A | 12/1995 | Klokkers-Bethke et al. | . | 424/468 |
| 5,556,940 A | 9/1996 | Willick et al. | | 530/317 |
| 5,602,100 A | 2/1997 | Brown et al. | | 514/18 |
| 5,614,219 A | 3/1997 | Wunderlich et al. | | 424/472 |
| 5,693,616 A | 12/1997 | Krstenansky et al. | | 514/12 |
| 5,766,620 A | 6/1998 | Heiber et al. | | 424/436 |
| 5,807,746 A | 9/1998 | Lin et al. | | 435/375 |
| 5,912,014 A | 6/1999 | Stern et al. | | 424/474 |
| 5,955,425 A | 9/1999 | Morley et al. | | 514/11 |
| 5,968,895 A | 10/1999 | Gefter et al. | | 514/2 |
| 6,086,918 A | 7/2000 | Stern et al. | | 424/474 |
| 6,110,892 A | 8/2000 | Barbier et al. | | 514/11 |
| 6,210,925 B1 | 4/2001 | Mehta et al. | | 435/69.1 |
| 6,242,495 B1 | 6/2001 | Leone-Bay et al. | | 514/617 |
| 6,248,558 B1 | 6/2001 | Lin et al. | | 435/69.1 |
| 6,673,574 B2 | 1/2004 | Stern et al. | | 435/69.7 |
| 2003/0091507 A1* | 5/2003 | Holst et al. | | 424/9.2 |
| 2003/0104981 A1* | 6/2003 | Mandic | | 514/3 |
| 2003/0134896 A1* | 7/2003 | Eustache et al. | | 514/475 |
| 2004/0023882 A1* | 2/2004 | Peri et al. | | 514/12 |
| 2004/0197323 A1 | 10/2004 | Mehta et al. | | 424/130.1 |
| 2005/0079145 A1* | 4/2005 | Constantinides et al. | . | 424/70.11 |

FOREIGN PATENT DOCUMENTS

| | | |
|---|---|---|
| AU | A-79394/87 | 4/1988 |
| CA | 2126299 | 12/1995 |
| EP | 0 162 764 | 11/1985 |
| EP | 0 308 067 | 3/1989 |
| EP | 0 382 403 | 8/1990 |
| EP | 0 489 217 | 6/1992 |
| EP | 0 517 211 | 12/1992 |
| EP | 0 263 493 | 4/1998 |
| EP | 0 878 201 | 11/1998 |
| EP | 878201 A1 * | 11/1998 |
| EP | 0 920 873 | 6/1999 |
| EP | 0 926 158 | 6/1999 |
| EP | 1 059 933 | 1/2003 |
| JP | 56-140924 | 4/1981 |
| WO | WO 91/14454 | 10/1991 |
| WO | WO 93/06845 | 4/1993 |
| WO | WO 95/25534 | 9/1995 |
| WO | WO95/28963 | 11/1995 |
| WO | WO 95/34295 | 12/1995 |
| WO | WO 96/35447 | 11/1996 |
| WO | WO 97/33531 | 9/1997 |
| WO | WO 99/18945 | 4/1999 |
| WO | WO 99/31137 | 6/1999 |
| WO | WO 99/43708 | 9/1999 |
| WO | WO 99/64449 | 12/1999 |
| WO | WO 00/07979 | 2/2000 |
| WO | WO 00/10596 | 3/2000 |
| WO | WO 00/31137 | 6/2000 |

(Continued)

OTHER PUBLICATIONS

A. Schally. Aspects of Hypothalamic Regulation of the Pituitary Gland . . . Nobel Lecture. Dec. 8, 1977, pp. 405-438.*
Neugebauer et al. Solution Structure and Adenylyl Cyclase Stimulating Activities . . . Biochemistry. 1995, vol. 34, No. 27, pp. 8835-8842.*
Seiya Kagatani, et al., "Enhancement of Nasal Salmon Calcitonin Absorption by Lauroylcarnitine Chloride in Rats", *Pharmaceutical Research*, vol. 13, No. 5, pp. 739-743, 1996.
Bruce Aungst, "Novel Formulation Strategies for Improving Oral Bioavailability of Drugs with Poor Membrane Permeation or Prysystemic Metabolism", *Journal of Pharmaceutical Sciences*, vol. 82, No. 10, pp. 979-987, Oct. 1993.
Charles M. Lang, et al.,"Effects of glucose-insulin-postassium on intestinal hemodynamics and substrate utilization during endotoxemia", *American Physiological Society*, 251(3Pt 1):341-8 (1996).
Joseph A. Fix, et al., "Acylcarnitines: drug absorption-enhancing agents in the gastrointestinal tract", *American Physiological Society*, 251(3 Pt 1):332-40 (1986).
Takayuki Ohwaki, et al., "Effects of Dose, pH, and Osmolarity on Nasal Absorption of Secretin in Rats II: Histological Aspects of the Nasal Mucosa in Relation to the Absorption Variation Due to the Effects of pH and Osmolarity", *Journal of Pharmaceutical Sciences*, vol. 76, No., pp. 695-697, Sep. 1987.

(Continued)

*Primary Examiner* — Jeffrey E Russel
(74) *Attorney, Agent, or Firm* — Greenberg Traurig, LLP; David J. Dykeman; Danielle T. Abramson

(57) ABSTRACT

Bioavailability of peptide active agents to be administered orally is enhanced by a pharmaceutical composition providing an active peptide that is amidated at a site that is not naturally amidated.

42 Claims, No Drawings

FOREIGN PATENT DOCUMENTS

| WO | WO 01/21198 | 3/2001 |
|---|---|---|
| WO | WO 01/22093 | 3/2001 |
| WO | WO 01/27154 | 4/2001 |
| WO | WO 01/36039 | 5/2001 |
| WO | WO 01/44199 | 6/2001 |
| WO | WO 01/68112 | 9/2001 |
| WO | WO 01/81415 | 11/2001 |
| WO | WO 02/043767 | 6/2002 |

OTHER PUBLICATIONS

Doris A. Stoffers, et al. "Multiple Forms of Rat Peptidyl-Glycine α-Amidating Monooxygenase", *Advances in Gene Technology: Molecular Neurobiology and Neuropharmacology*, ICSU Short Reports ,vol. 9, p. 120, 1989.

J. Lai-Sim Au, "Disposition and Availability of 5-Fluorouracil Prodrug 5'-Deoxy-5-fluorourdine after Oral Administration in Rats", *Journal of Pharmaceutical Sciences*, vol. 76, p. 699, Sep. 1987.

Willa A. Hsueh, Proteases in Hormone Production and Metabolism, pp. 141-151.

Alan F. Bradbury, et al., "Peptide Amidation: Evidence for Multiple Molecular Forms of the Amidating Enzyme" *Biochemical and Biophysical Research Communications*, vol. 154, No. 3, pp. 1293-1300, Aug. 15, 1988.

Vector Pharma Ongoing Research "Oral Delivery of Peptides", 1996.

Peter Langguth, et al., "Oral Absorption of Peptides: The Effect of Absorption Site and Enzyme Inhibition on the Systemic Availability of Metkephanid" *Pharmaceutical Research*, vol. 11(4):528-535, Nov. 1994.

Martha V.L. Ray, et al., "Production of Recombinant Salmon Calcitonin by In Vitro Amidation of an *Escherichia coli* Produced Precursor Peptide", *Biotechnology*, vol. 11, pp. 64-70, Jan. 1993.

James F. Whitfield, Ph.D., et al., "Adenylyl Cyclase-Activating Anabolic Agents: Pararoid Hormone and Prostaglandins E", *Anabolic Treatments for Osteoporosis*, Chapter 5, pp. 109-149 (1998).

Betty A. Eipper, et al., The Biosynthesis of Neuropeptides: Peptide α-Amidation, Annu. Rev. Neurosci, 15:57-85 (1992).

David J. Merkler,"C-Terminal amidated peptides: Production by the in vitro enzymatic amidation of glycine-extended peptides and the importance of the amide to bioactivity", *Enzyme Microb. Technol.*, vol. 16, Jun. 1994.

Tania Fernandez, et al., "Ferrying proteins to the other side", *Nature Biotechnology*, vol. 16 May 1998.

Andreas Bernkop-Schnürch, "The use of inhibitory agents to overcome the enzymatic barrier to perorally administered therapeutic peptides and proteins", *Journal of Controlled Release*, 52(1998) 1-16.

Dinesh Patel et al.,"Peptide Targeting and Delivery across the Blood—Brain Barrier Utilizing Synthetic Triglyceride Esters: Design, Synthesis, and Bioactivity", *Bioconjugate Chem.*, 1997, 8, 434-441.

H. Rico et al.: "Salmon Calcitonin Versus man Calcitonin Paget's Disease of Bone", *Current Therapeutic Research*, vol. 49, No. 1 Jan. 1991, Abstract.

E. Scott Swenson and William J. Curatolo, *Advanced Drug Delivery Reviews* (1992) 39-92, "(C) Means to Enhance Penetration (2) Intestinal permeability enhancement for proteins, peptides and other polar drugs: mechanisms and potential toxicity".

Remington's Pharmaceutical Sciences, 18th Edition, pp. 1319, 1634-38 (1990).

International Search Report dated Nov. 5, 2004.

European Search Report dated Aug. 30, 2005.

International Search Report dated Oct. 26, 2005.

Takahashi, Ken-Ichiro et al.: "Production of Bioactive Salmon Calcitonin From the Nonendocrine Cell Lines COS-7 and CHO", Peptides, vol. 18, No. 3, pp. 439-444, 1997, XP002341274 ISSN: 0196-9781/97.

Lu Jun et al.: "TAP-Independent Presentation 1 of CTL Epitopes by Trojan Antigens", Journal of Immunology, vol. 166, No. 12, pp. 7063-7071, Jun. 15, 2001, XP002341273, ISSN: 0022-1767/01.

Erickson and Merrifield, "Solid Phase Peptide Synthesis", vol. II, Chapter 3, pp. 255-527 *The Proteins*, Third Edition, Neurath et al, Eds., Academic Press, New York, 1976.

Hodges, R.S. et al. "Protein Design Using Model Synthetic Peptides", *Peptide Research*, vol. 1, No. 1, pp. 19-30 (1988).

Atherton, E. and Sheppard, R.C., "Solid Phase Peptide Synthesis—The Merrifield Technique", *Solid Phase Peptide Synthesis a Practical Approach*, Chapter 2, pp. 13-23, IRL Press, Oxford University Press (1989).

Jouishomme et al., "Further Definition of the Protein Kinase C Activation Domain of the Parathyroid Hormone", *J. Bone Miner. Res.*, vol. 9, No. 6, pp. 943-949 (1994).

Rixon, R.H. et al., "Parathyroid Hormone Fragments May Stimulate Bone Growth in Ovariectomized Rats by Activating Adenylyl Cyclase", *J. Bone Miner. Res.*, vol. 9, No. 8, pp. 1179-1189 (1994).

Whitfield, J.F. et al., "Stimulation of the Growth of Femoral Trabecular Bone in Ovariectomized Rats by the Novel Parathyroid Hormone Fragment, hPTH-(1-31)NH$_2$ (Ostabolin)", *Calcified Tissue Int.*, 58:81-87 (1996).

Schwarz, S.R. et al., "In Vivo Protein Transduction: Delivery of a Biologically Active Protein into the Mouse", *Science*, 285:1569-1572 (Sep. 3, 1999).

Zhang, L. et al., "Preparation of Functionally Active Cell-Permeable Peptides by Single-Step Ligation of Two Peptide Modules", *Proc. Natl. Acad. Sci.* 95:9184-9189 (Aug. 1998).

Phelan, A. et al. "Intercellular Delivery of Functional p53 By The Herpesvirus Protein VP22", *Nature Biotechnology*, 16:440-443 (May 1998).

Rojas, M. et al., "Genetic Engineering of Proteins With Cell Membrane Permeability", *Nature Biotechnology*, 16:370-375 (Apr. 1998).

Merrifield, R.B., "Solid Phase Peptide Synthesis. I. The Synthesis of a Tetrapeptide", *J. Am. Chem. Soc.*, 85:2149-2154 (1-963).

Lin et al., "Synthesis of a Biological Active Tumor Growth Factor from the Predicted DNA Sequence of Shope Fibroma Virus", *Biochemistry*, 27:5640-5645 (1988).

Sambrook et al., Molecular Cloning: A Laboratory Manual, 2nd Ed., Cold Spring Harbor Laboratory, Cold Spring Harbor, N.Y. (1989).

Walter, G. et al, "Antibodies Specific for the Carboxy- and Amino-Terminal Regions of Simian Virus 40 Large Tumor Antigen", *Proc. Natl. Acad. Sci. USA*, vol. 77, No. 9, pp. 5197-5200 (Sep. 1980).

Goodfriend et al., "Antibodies to Bradykinin and Angiotensin: A Use of Carbodiimides to Immunology", *Science* vol. 144, pp. 1344-1346 (Jun. 1964).

D.C. Liebisch et at., "Isolation and structure of a C-terminally amidated nonopioid peptide, amidorphin-(8-26), from bovine striatum: A major product of proenkephalin in brain but not in adrenal medula", Proc. Natl. Acad. Sci. USA, vol. 83, pp. 1936-1940, Mar. 1986 Neurobiology.

Supplementary European Search Report dated Apr. 4, 2011 in corresponding European Application No. EP 04 70 4114.

Tomoyuki Sakai, et al., "Synthesis of Parathyroid Hormone-related Protein Analogs and Their Antagonistic Activities," Peptide Chemistry, Mino, Osaka, Japan, pp. 393-396, (Jan. 1, 1994).

Bassem Y. Azizeh, et al., "[des His[1], des Phe[6], Glu[9]] Glucagon Amide: A Newly Designed 'Pure' Glucagon Antagonist," Bioorganic & Medicinal Chemistry Letters, Pergamon, Elsevier Science, Great Britain, vol. 5, No. 16, pp. 1849-1852 (Aug. 17, 1995).

Noel S. Sturm, et al., "Structure-Function Studies on Positions 17, 18, and 21 Replacement Analogues of Glucagon: The Importance of Charged Residues and Salt Bridges in Glucagon Biological Activity," Journal of Medicinal Chemistry, vol. 41, pp. 2693-2700 (1998).

\* cited by examiner

```
                      SEQUENCE LISTING

<160> NUMBER OF SEQ ID NOS: 23

<210> SEQ ID NO 1
<211> LENGTH: 33
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn

<210> SEQ ID NO 2
<211> LENGTH: 31
<212> TYPE: PRT
<213> ORGANISM: Homo sapiens

<400> SEQUENCE: 2

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val
            20                  25                  30

<210> SEQ ID NO 3
<211> LENGTH: 26
<212> TYPE: PRT
<213> ORGANISM: Kaposi's sarcoma-associated herpesvirus

<400> SEQUENCE: 3

Ala Ala Val Ala Leu Leu Pro Ala Val Leu Leu Ala Leu Leu Ala Pro
1               5                   10                  15

Val Asn Arg Lys Arg Asn Lys Leu Met Pro
            20                  25

<210> SEQ ID NO 4
<211> LENGTH: 11
<212> TYPE: PRT
<213> ORGANISM: Human immunodeficiency virus
```

-continued

```
<400> SEQUENCE: 4

Tyr Gly Arg Lys Lys Arg Arg Gln Arg Arg Arg
1               5                   10

<210> SEQ ID NO 5
<211> LENGTH: 15
<212> TYPE: PRT
<213> ORGANISM: Homo sapiens

<400> SEQUENCE: 5

Val Thr Val Leu Ala Leu Gly Ala Leu Ala Gly Val Gly Val Gly
1               5                   10                  15

<210> SEQ ID NO 6
<211> LENGTH: 12
<212> TYPE: PRT
<213> ORGANISM: Kaposi's sarcoma-associated herpesvirus

<400> SEQUENCE: 6

Ala Ala Val Leu Leu Pro Val Leu Leu Ala Ala Pro
1               5                   10

<210> SEQ ID NO 7
<211> LENGTH: 5
<212> TYPE: PRT
<213> ORGANISM: Unknown
<220> FEATURE:
<223> OTHER INFORMATION: Target fragment of Caspase-1
<220> FEATURE:
<221> NAME/KEY: misc_feature
<222> LOCATION: (5)..(5)
<223> OTHER INFORMATION: Xaa can be any naturally occurring amino acid

<400> SEQUENCE: 7

Tyr Val Ala Asp Xaa
1               5

<210> SEQ ID NO 8
<211> LENGTH: 5
<212> TYPE: PRT
<213> ORGANISM: Unknown
<220> FEATURE:
<223> OTHER INFORMATION: Target fragment of Caspase-3
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 8

Asp Xaa Xaa Asp Xaa
1               5

<210> SEQ ID NO 9
<211> LENGTH: 5
<212> TYPE: PRT
<213> ORGANISM: Unknown
<220> FEATURE:
<223> OTHER INFORMATION: Target fragment of proprotein convertase 1
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
```

-continued

```
<400> SEQUENCE: 9

Arg Xaa Xaa Arg Xaa
1               5

<210> SEQ ID NO 10
<211> LENGTH: 5
<212> TYPE: PRT
<213> ORGANISM: Unknown
<220> FEATURE:
<223> OTHER INFORMATION: Target fragment of proprotein convertase 1
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 10

Lys Xaa Xaa Arg Xaa
1               5

<210> SEQ ID NO 11
<211> LENGTH: 6
<212> TYPE: PRT
<213> ORGANISM: Unknown
<220> FEATURE:
<223> OTHER INFORMATION: Target fragment of proprotein convertase 4
<220> FEATURE:
<221> NAME/KEY: misc_feature
<222> LOCATION: (6)..(6)
<223> OTHER INFORMATION: Xaa can be any naturally occurring amino acid

<400> SEQUENCE: 11

Gly Arg Thr Lys Arg Xaa
1               5

<210> SEQ ID NO 12
<211> LENGTH: 5
<212> TYPE: PRT
<213> ORGANISM: Unknown
<220> FEATURE:
<223> OTHER INFORMATION: Target fragment of proprotein convertase 4
      PACE 4
<220> FEATURE:
<221> NAME/KEY: misc_feature
<222> LOCATION: (5)..(5)
<223> OTHER INFORMATION: Xaa can be any naturally occurring amino acid

<400> SEQUENCE: 12

Arg Val Arg Arg Xaa
1               5

<210> SEQ ID NO 13
<211> LENGTH: 5
<212> TYPE: PRT
<213> ORGANISM: Unknown
<220> FEATURE:
<223> OTHER INFORMATION: Target fragment of proprotein convertase 4
      PACE 4
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Arg Val Arg Arg Xaa
1               5
```

```
<210> SEQ ID NO 14
<211> LENGTH: 4
<212> TYPE: PRT
<213> ORGANISM: Unknown
<220> FEATURE:
<223> OTHER INFORMATION: Target fragment of Endothelin cleaving enzyme
      followed by dipeptidyl-peptidase IV
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Trp Val Pro Xaa
1

<210> SEQ ID NO 15
<211> LENGTH: 4
<212> TYPE: PRT
<213> ORGANISM: Unknown
<220> FEATURE:
<223> OTHER INFORMATION: Target fragment of Endothelin cleaving enzyme
      followed by dipeptidyl-peptidase IV
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Trp Val Ala Xaa
1

<210> SEQ ID NO 16
<211> LENGTH: 4
<212> TYPE: PRT
<213> ORGANISM: Unknown
<220> FEATURE:
<223> OTHER INFORMATION: Target fragment of Neprilysin followed by
      dipeptidyl-peptidase IV
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 16

Xaa Phe Xaa Xaa
1

<210> SEQ ID NO 17
<211> LENGTH: 4
<212> TYPE: PRT
<213> ORGANISM: Unknown
<220> FEATURE:
<223> OTHER INFORMATION: Target fragment of Neprilysin followed by
      dipeptidyl-peptidase IV
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 17

Xaa Tyr Xaa Xaa
1
```

```
<210> SEQ ID NO 18
<211> LENGTH: 4
<212> TYPE: PRT
<213> ORGANISM: Unknown
<220> FEATURE:
<223> OTHER INFORMATION: Target fragment of Neprilysin followed by
      dipeptidyl-peptidase IV
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 18

Xaa Trp Xaa Xaa
1

<210> SEQ ID NO 19
<211> LENGTH: 12
<212> TYPE: PRT
<213> ORGANISM: Unknown
<220> FEATURE:
<223> OTHER INFORMATION: Target fragment of Renin followed by
      dipeptidyl-peptidase IV

<400> SEQUENCE: 19

Asp Arg Tyr Ile Pro Phe His Leu Leu Val Tyr Ser
1               5                   10

<210> SEQ ID NO 20
<211> LENGTH: 7
<212> TYPE: PRT
<213> ORGANISM: Unknown
<220> FEATURE:
<223> OTHER INFORMATION: Target fragment of proprotein convertase 1
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 20

Arg Xaa Xaa Xaa Xaa Arg Xaa
1               5

<210> SEQ ID NO 21
<211> LENGTH: 9
<212> TYPE: PRT
<213> ORGANISM: Unknown
<220> FEATURE:
<223> OTHER INFORMATION: Target fragment of proprotein convertase 1
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 21

Arg Xaa Xaa Xaa Xaa Xaa Xaa Arg Xaa
1               5

<210> SEQ ID NO 22
```

```
<211> LENGTH: 7
<212> TYPE: PRT
<213> ORGANISM: Unknown
<220> FEATURE:
<223> OTHER INFORMATION: Target fragment of proprotein convertase 1
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Lys Xaa Xaa Xaa Xaa Arg Xaa
1               5

<210> SEQ ID NO 23
<211> LENGTH: 9
<212> TYPE: PRT
<213> ORGANISM: Unknown
<220> FEATURE:
<223> OTHER INFORMATION: Target fragment of proprotein convertase 1
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 23

Lys Xaa Xaa Xaa Xaa Xaa Xaa Arg Xaa
1               5
```

ORAL DELIVERY OF PEPTIDES

RELATED APPLICATION

This application is based upon and claims priority to U.S. Provisional Application Ser. No. 60/441,856, filed Jan. 21, 2003.

BACKGROUND OF THE INVENTION

1. Field of the Invention

The present invention relates to orally administered peptide pharmaceuticals where the active compounds include a plurality of amino acids and at least one peptide bond in their molecular structures, and to methods of enhancing bioavailability of such peptide active compounds when administered orally.

2. Description of the Related Art

Numerous human hormones, neurotransmitters, cytokines, growth factors and other important biological compounds have peptides as a substantial part of their molecular structures. Many diseases respond positively to raising the level of these peptide compounds in patients. Therapeutically effective amounts of such biologically relevant peptides may be administered to patients in a variety of ways. However, as discussed further below, preferred oral administration is very difficult with this type of active compound.

Salmon calcitonin, for example, is a peptide hormone which decreases calcium release from bone. When used to treat bone-related diseases and calcium disorders (such as osteoporosis, Paget's disease, hypercalcemia of malignancy, and the like), it has the effect of helping maintain bone density. Many types of calcitonin have been isolated (human calcitonin, salmon calcitonin, eel calcitonin, elkatonin, porcine calcitonin, and chicken calcitonin). There is significant structural non-homology among the various calcitonin types. For example, there is only 50% percent identity between the amino acids making up human calcitonin and those making up salmon calcitonin. Notwithstanding the difference in molecular structure, salmon calcitonin may be used in the human treatment of the calcitonin-responsive diseases discussed above.

Another example of peptide hormone is parathyroid hormone(PTH). PTH is produced by the parathyroid gland and is a major regulator of blood calcium levels. PTH is a polypeptide and synthetic polypeptides may be prepared by the method disclosed by Erickson and Merrifield, The Proteins, Neurath et al, Eds., Academic Press, New York, 1976, page 257, and as modified by the method of Hodges et al (1988), Peptide Research 1, 19, or by Atherton, E. and Sheppard, R. C., Solid Phase Peptide Synthesis, IRL Press, Oxford, 1989.

When serum calcium is reduced to below a normal level, the parathyroid gland releases PTH and the calcium level is increased by resorption of bone calcium, by increased absorption of calcium from the intestine, and by increased renal reabsorption of calcium from nascent urine in the kidney tubules. Although continuously infused low levels of PTH can remove calcium from the bone, the same low doses, when intermittently injected can actually promote bone growth.

Tregear, U.S. Pat. No. 4,086,196, described human PTH analogues and claimed that the first 27 to 34 amino acids are the most effective in terms of the stimulation of adenylyl cyclase in an in vitro cell assay. Rosenblatt, U.S. Pat. No. 4,771,124, disclosed the property of hPTH analogues wherein $Trp^{23}$ is substituted by amino acids phenylalanine, leucine, norleucine, valine, tyrosine, β-naphthylalanine, or α-naphthylalanine as a PTH antagonist. These modified hPTH analogues also have the 2 and 6 amino terminal acids removed, resulting in loss of most agonist activities when used to treat osteoporosis. These analogues were designed as inhibitors of PTH and PTH-related peptides. The analogues were claimed as possibly useful in the treatment of hypercalcemia associated with some tumors.

Pang et al, WO93/06845, published Apr. 15, 1993, described analogues of hPTH which involve substitutions of $Arg^{25}$, $Lys^{26}$, $Lys^{27}$ with numerous amino acids, including alanine, asparagine, aspartic acid, cysteine, glutamine, glutamic acid, glycine, histidine, isoleucine, leucine, methionine, phenylalanine, proline, serine, threonine, tryptophan, tyrosine, or valine. These are claimed to be effective in the treatment of osteoporosis with minimal effects on blood pressure and smooth muscle.

PTH operates through activation of two second messenger systems, $G_s$-protein activated adenylyl cyclase (AC) and $G_q$-protein activated phospholipase $C_β$. The latter results in a stimulation of membrane-bound protein kinase Cs (PKC) activity. The PKC activity has been shown to require PTH residues 29 to 32 (Jouishomme et al (1994) J. Bone Mineral Res. 9, (1179-1189). It has been established that the increase in bone growth, i.e., that effect which is useful in the treatment of osteoporosis, is coupled to the ability of the peptide sequence to increase AC activity. The native PTH sequence has been shown to have all of these activities. The human hPTH-(1-34) sequence is typically shown as:

Ser Val Ser Glu Ile Gln Leu Met His Asn Leu Gly Lys His Leu Asn Ser Met Glu Arg Val Glu Trp Leu Arg Lys Lys Leu Gln Asp Val His Asn Phe-OH (SEQ ID NO:1).

Various PTH analogues are disclosed in U.S. Pat. Nos. 5,955,425 and 6,110,892. The following linear analogue (truncated hPTH), hPTH-(1-31)-$NH_2$, has only AC-stimulating activity and has been shown to be fully active in the restoration of bone loss in the ovariectomized rat model (Rixon, R. H. et al (1994) J. Bone Miner. Res. 9, 1179-1189; Whitfield et al (1996), Calcified Tissue Int. 58, 81-87; and Willick et al, U.S. Pat. No. 5,556,940):

Ser Val Ser Glu Ile Gln Leu Met His Asn Leu Gly Lys His Leu Asn Ser Met Glu Arg Val Glu Trp Leu Arg Lys Lys Leu Gin Asp Val-$NH_2$(SEQ ID NO:2).

Peptide pharmaceuticals used in the prior art frequently have been administered by injection or by nasal administration. Insulin is one example of a peptide pharmaceutical frequently administered by injection. A more preferred and convenient oral administration tends to be problematic because peptide active compounds are very susceptible to degradation in the stomach and intestines. For example, while the prior art has reported an ability to achieve reproducible blood levels of salmon calcitonin and parathyroid hormone when administered orally, these levels are low. This is believed to be because these peptide hormones lack sufficient stability in the gastrointestinal tract, and tend to be poorly transported through intestinal walls into the blood. However, injection and nasal administration are significantly less convenient than, and involve more patient discomfort than, oral administration. Often this inconvenience or discomfort results in substantial patient noncompliance with a treatment regimen. Thus, there is a need in the art for more effective and reproducible oral administration of peptide pharmaceuticals like insulin, salmon calcitonin, parathyroid hormone and others discussed in more detail herein.

Proteolytic enzymes of both the stomach and intestines may degrade peptides, rendering them inactive before they can be absorbed into the bloodstream. Any amount of peptide that survives proteolytic degradation by proteases of the stomach (typically having acidic pH optima) is later confronted with proteases of the small intestine and enzymes secreted by the pancreas (typically having neutral to basic pH optima). Specific difficulties arising from the oral administration of a peptide like salmon calcitonin involve the relatively large size of the molecule, and the charge distribution it carries. This may make it more difficult for salmon calcitonin to penetrate the mucus along intestinal walls or to cross the intestinal brush border membrane into the blood.

One way to improve the effectiveness of oral administration of peptides is to protect them from proteolytic enzymes in the stomach and intestine as well as enhance their absorption from the intestine thereby enhancing their bioavailability. Improving oral effectiveness is important for several reasons. First, peptides and proteins are expensive to manufacture either by chemical synthesis or recombinant DNA technologies. Therefore, the more one increases bioavailability, the lesser the amounts that will be required in an oral formulation of a therapeutic drug.

Second, the greater the bioavailability of an oral peptide, the less the variability in the dosage absorbed by an individual on a day to day basis.

Third, the greater the bioavailability of an oral peptide, the less the concern about breakdown products of the peptide since such breakdown products can act as agonists or antagonists of the receptors where the peptide binds to elicit biological activity.

SUMMARY OF THE INVENTION

It is accordingly an object of the present invention to provide a therapeutically effective oral pharmaceutical composition for reliably delivering pharmaceutical peptides, e.g., physiologically active peptide agents such as insulin, salmon calcitonin, parathyroid hormone, vasopressin, or analogs thereof and others discussed herein.

It is a further object of the invention to provide therapeutic methods for enhancing the bioavailability of such peptides.

It is a further object of the invention to provide methods of treating bone-related diseases and calcium disorders by administering salmon calcitonin or PTH 1-31NH$_2$ orally.

In one aspect, the invention provides a pharmaceutical composition for oral delivery of a physiologically active peptide agent comprising a therapeutically effective amount of said active peptide, wherein said active peptide is amidated at a location that is not naturally amidated.

Preferred peptide active agents include but are not limited to insulin, vasopressin, salmon calcitonin, glucagon-like peptide 1 or 2, parathyroid hormone, luteinizing hormone releasing hormone, erythropoeitin, and analogs thereof. Especially preferred is parathyroid hormone and analogs thereof.

In another aspect, the invention provides a method for enhancing the bioavailability of a therapeutic peptide active agent delivered orally, said method comprising amidating said peptide agent.

The present invention is believed to reduce the likelihood of proteolytic degradation of the peptide active compound by simultaneously protecting the peptide from proteolytic attack by (1) stomach proteases which are typically most active at acidic pHs and (2) intestinal or pancreatic proteases (which are typically most active at basic to neutral pH).

Also, the invention is believed to promote the process by which the peptide crosses the intestinal brush border membrane into the blood due to the presence of amide, while continuing to protect the peptide from proteolytic degradation.

An acid resistant protective coating of the capsule or tablet protects the peptide active agent from the acid-acting proteases of the stomach. Thereafter, after the formulation passes into the intestine where the pH is less acidic, the enteric coating dissolves to release the contents of the formulation. Significant quantities of acid (with which the peptide active agent is intermixed) reduce the activity of neutral to basic-acting proteases (e.g., luminal or digestive proteases and proteases of the brush border membrane) by lowering pH locally at the site of release of the formulation below their optimal activity range.

Other features and advantages of the present invention will become apparent from the following detailed description of the invention.

DETAILED DESCRIPTION OF THE INVENTION

In accordance with the invention, patients in need of treatment with peptide active ingredients are provided with an oral pharmaceutical composition thereof (at appropriate dosage), preferably but not necessarily in tablet or capsule form of an ordinary size in the pharmaceutical industry. The dosages and frequency of administering the products are discussed in more detail below. Patients who may benefit are any who suffer from disorders that respond favorably to increased levels of a peptide-containing compound. For example, oral salmon calcitonin in accordance with the invention may be used to treat patients who suffer from calcium disorders or bone diseases. The invention may be used, for example, to treat osteoporosis, Paget's disease, hypercalcemia of malignancy and the like, with oral calcitonin, oral parathyroid hormone, preferably hPTH 1-31NH$_2$ and hPTH 1-34NH$_2$.

Salmon calcitonin is a preferred active ingredient for use in accordance with the invention for a number of reasons. For example, it provides a number of advantages over even human calcitonin, even though used as a pharmaceutical agent for human patients. Among the advantages provided by utilizing salmon calcitonin instead of human calcitonin for the treatment of human osteoporosis are increased potency, analgesia and increased half-life. Salmon calcitonin is more effective than natural human calcitonin in treatment, since lower dosages are necessary than with human calcitonin. There is substantial non-homology between salmon and human calcitonin, with only 50% identity in the amino acid sequences of the two calcitonins.

Without intending to be bound by theory, the pharmaceutical composition of the invention is believed to overcome a series of different and unrelated natural barriers to bioavailability. Various components of the pharmaceutical compositions act to overcome different barriers by mechanisms appropriate to each, and result in synergistic effects on the bioavailability of a peptide active ingredient.

The peptide active compound may be administered orally. In accordance with the invention, the presence of at least one amide group would protect the peptide or protein from proteolytic degradation, thereby improving bioavailability. The amide group may also enhance the membrane permeability of the protein across the lumen of the intestine. Other mechanisms for increase in bioavailability by the presence of the amide group may also be possible.

Various techniques exist for recombinant production of peptide products, i.e. any compound whose molecular structure includes a plurality of amino acids linked by a peptide bond.

Overview of a Preferred Expression Vector

A preferred expression vector is described in U.S. Pat. No. 6,210,925 and is incorporated herein by reference. An example of a preferred vector for expressing salmon calcitonin is shown in FIG. 9 of U.S. Pat. No. 6,210,925. For the expression of other peptide products, a nucleic coding for the desired peptide product would be substituted for the nucleic acid coding for salmon calcitonin.

The preferred expression vector comprises a coding region and a control region. The coding region comprises nucleic acids for a peptide product of interest coupled in reading frame downstream from nucleic acids coding for a signal peptide. The control region is linked operably to the coding region and comprises a plurality of promoters and at least one ribosome binding site, wherein at least one of the promoters is selected from the group consisting of tac and lac.

Preferably, the vector comprises a plurality of transcription cassettes placed in tandem, each cassette having the control region and the coding region of the present invention. Such a digenic vector or multigenic vector is believed to provide better expression than would a dicistronic or multicistronic expression vector. This is a surprising improvement over dicistronic or multicistronic expression which is not believed to be suggested by the prior art.

The vector can optionally further comprise nucleic acids coding for a repressor peptide which represses operators associated with one or more of the promoters in the control region, a transcription terminator region, a selectable marker region and/or a region encoding at least one secretion enhancing peptide. Alternatively, in some embodiments, nucleic acids coding for a repressor peptide and a secretion enhancing peptide may be present on a separate vector co-expressed in the same host cell as the vector expressing the peptide product.

Many commercially available vectors may be utilized as starting vectors for the preferred vectors of the invention. Some of the preferred regions of the vectors of the invention may already be included in the starting vector such that the number of modifications required to obtain the vector of the invention is relatively modest.

The Control Region

The control region is operably linked to the coding region and comprises a plurality of promoters and at least one ribosome binding site, wherein at least one of the promoters is selected from the group consisting of lac and tac. The foregoing combination of promoters in a single control region significantly increases yield of the peptide product produced by the coding region (as described in more detail intra). Other promoters are known in the art, and may be used in combination with a tac or lac promoter. Such promoters include but are not limited to lpp, ara B, trpE, gal K.

Preferably, the control region comprises exactly two promoters. When one of the promoters is tac, it is preferred that the tac promoter be 5' of another promoter in the control region. When one of the promoters is lac, the lac promoter is preferably 3' of another promoter in the control region. Also preferably, the control region comprises both a tac promoter and a lac promoter, preferably with the lac promoter being 3' of the tac promoter.

The Coding Region

The coding region comprises nucleic acids coding for a peptide product of interest coupled in reading frame downstream from nucleic acids coding for a signal peptide whereby the coding region encodes a peptide comprising, respectively, from N terminus to C terminus the signal and the peptide product. Without intending to be bound by theory, it is believed that the signal may provide some protection to the peptide product from proteolytic degradation in addition to participating in its secretion to the periplasm.

Many peptide signal sequences are known and may be used in accordance with the invention. These include signal sequences of outer membrane proteins of well-characterized host cells, and any sequences capable of translocating the peptide product to the periplasm and of being post-translationally cleaved by the host as a result of the translocation. Useful signal peptides include but are not limited to Omp A, pel B, Omp C, Omp F, Omp T, βla, Pho A, Pho S and Staph A.

The peptide product is preferably small enough so that it would usually require a fusion partner using prior art technology. Typically, the peptide product has a molecular weight of less than 10 KDa. More preferably, the peptide product has a C-terminal glycine, and is used as a precursor to an enzymatic amidation reaction converting the C-terminal glycine to an amino group, thus resulting in an amidated peptide. Such a conversion is described in more detail infra. Numerous biologically important peptide hormones and neurotransmitters are amidated peptides of this type. For example, the peptide product coded by the coding region may be salmon calcitonin precursor or calcitonin gene related peptide precursor, both of which have C-terminal glycines and both of which may be enzymatically amidated to mature salmon calcitonin or mature calcitonin gene related peptide.

Analogs of parathyroid hormone could also be produced in accordance with the invention. For example, a peptide having the first 34 amino acids of parathyroid hormone can provide a function similar to that of parathyroid hormone itself, as may an amidated version of the 34 amino acid analog. The latter may be produced by expressing, in accordance with one or more of the expression systems and methods described herein, the first 34 amino acids of parathyroid hormone, followed by glycine-35. Enzymatic amidation as disclosed herein could then convert the glycine to an amino group.

Other Optional Aspects of a Preferred Vector of the Invention or of Other Vectors to be Expressed in the Same Host as the Vector of the Invention Repressor Optionally, the preferred vector may contain nucleic acids coding for a repressor peptide capable of repressing expression controlled by at least one of the promoters. Alternatively, however, the nucleic acids coding for a repressor peptide may be present on a separate vector in a host cell with the vector of the present invention. Appropriate repressors are known in the art for a large number of operators. Preferably, the nucleic acids coding for the repressor encode a lac repressor in preferred embodiments of the invention because it represses the lac operator that is included with both tac and lac promoters, at least one of which promoters is always present in preferred vectors of the invention.

Selectable Marker

It is preferred that any of a large number of selectable marker genes (e.g. a gene encoding kanamycin resistance) be present in the vector. This will permit appropriate specific selection of host cells that are effectively transformed or transfected with the novel vector of the invention.

Secretion Enhancing Peptide

Nucleic acids coding for at least one secretion enhancing peptide are optionally present in the vector of the present invention. Alternatively, the nucleic acids coding for a secretion enhancing peptide may be present on a separate vector expressed in the same host cell as the vector encoding the peptide product. Preferably, the secretion enhancing peptide is selected from the group consisting of SecY (prlA) or prlA-4. It is pointed out that SecY and prlA are identical, the two terms being used as synonyms in the art. prlA-4 is a known modification of prlA and has a similar function. Another preferred secretion enhancing peptide is SecE also known as "prlG", a term used as a synonym for "SecE". Most preferably, a plurality of secretion enhancing peptides are encoded, at least one of which is SecE and the other of which is selected from the group consisting of SecY (prlA) and prlA-4. The two are believed to interact to aid translocation of the peptide product from cytoplasm to periplasm. Without intending to be bound by theory, these secretion enhancing peptides may help protect the peptide product from cytoplasmic proteases in addition to their secretion enhancing functions.

Amidation of peptides and proteins, preferably at the C-terminus, affords a significant increase in oral bioavailability as demonstrated hereinbelow. The prior art indicates that natural amidation of biologically active peptides may increase receptor binding and improve the stability of these peptides (Eipper et al., Annu. Rev. Neurosci., 15:57-85, 1992; Merkler, Enzyme Micob. Technol., 16:450-456, particularly page 51, 1994). The significant increase in bioavailability afforded by amidation of these peptides was unexpected, since current knowledge states that the primary determinants of oral bioavailability of peptides and proteins are the site, the secondary and tertiary structure, and the charge of the molecules.

Normally, the plasma membrane of eukaryotic cells is impermeable to large peptides or proteins. However, certain hydrophobic moieties such as amino acid sequences, fatty acids and bile acids variously called ferry peptides or membrane translocating sequences or moieties, when fused to the functional proteins or peptides, in particular to the N- or C-terminus, can act as membrane translocators, and mediate the transport of these proteins into living cells. These membrane translocators (MTs) for the purpose of the present invention are capable of being at least partially cleaved by a blood or lymphatic system protease.

In accordance with another aspect of the invention, the presence of at least one membrane translocator (MT), preferably two MTs, more preferably, two peptide MTs would enhance the membrane permeability of the peptide fused to the MT(s) across the lumen of the intestine and provide for improved bioavailability. Since the MT link to the active peptide can be cleaved by an enzyme in the blood or the lymphatic system, it leaves the active peptide free to reach its target.

Also, in accordance with the invention, proteolytic degradation of the peptide and of the membrane translocator by stomach enzymes (most of which are active in the acid pH range) and intestinal or pancreatic proteases (most of which are active in the neutral to basic pH range) is reduced.

Again, without intending to be bound by theory, it appears that, in accordance with the present invention, the peptide is transported through the stomach under the protection of an appropriate acid-resistant protective vehicle for substantially preventing contact between the salmon calcitonin or other active peptide and any stomach proteases capable of degrading it. Once the pharmaceutical composition of the invention passes through the stomach and enters the intestinal region where basic to neutral pH predominates, and where proteases tend to have basic to neutral pH optima, the enteric coating or other vehicle releases the peptide and acid or protease inhibitors (in close proximity to each other).

The acid is believed to lower the local intestinal pH (where the active agent has been released) to levels below the optimal range for many intestinal proteases and other intestinal enzymes. This decrease in pH reduces the proteolytic activity of the intestinal proteases, thus affording protection to the peptide and the membrane translocator from potential degradation. The activity of these proteases is diminished by the temporarily acidic environment provided by the invention. It is preferred that sufficient acid be provided that local intestinal pH is lowered temporarily to 5.5 or below, preferably 4.7 or below and more preferably 3.5 or below. The sodium bicarbonate test described below (in the section captioned "the pH-Lowering Agent") is indicative of the required acid amount. Preferably, conditions of reduced intestinal pH persist for a time period sufficient to protect the peptide agent and the membrane translocator from proteolytic degradation until at least some of the peptide agent has had an opportunity to cross the intestinal wall into the bloodstream. For salmon calcitonin, experiments have demonstrated a $T_{max}$ of 5-15 minutes for blood levels of salmon calcitonin when the active components are injected directly into the duodenum, ileum or colon of rats.

Alternatively, protease inhibitors are believed to reduce the proteolytic activity of the intestinal proteases, thus affording protection to the peptide and the membrane translocator from premature potential degradation.

Compositions of the present invention can optionally contain absorption enhancers. The absorption enhancers of the invention synergistically promote peptide absorption into the blood while conditions of reduced proteolytic activity prevail.

The mechanism by which the invention is believed to accomplish the goal of enhanced bioavailability is aided by having active components of the pharmaceutical composition released together as simultaneously as possible. To this end, it is preferred to keep the volume of enteric coating as low as possible consistent with providing protection from stomach proteases. Thus enteric coating is less likely to interfere with peptide release, or with the release of other components in close time proximity with the peptide. The enteric coating should normally add less than 30% to the weight of the remainder of pharmaceutical composition (i.e., the other components of the composition excluding enteric coating). Preferably, it is less than 20% and, more preferably, the enteric coating adds between 10% and 20% to the weight of the uncoated ingredients.

The absorption enhancer which may be a solubility enhancer and/or transport enhancer (as described in more detail below) aids transport of the peptide agent from the intestine to the blood, and may promote the process so that it better occurs during the time period of reduced intestinal pH and reduced intestinal proteolytic activity. Many surface active agents may act as both solubility enhancers and transport (uptake) enhancers. Again without intending to be bound by theory, it is believed that enhancing solubility provides (1) a more simultaneous release of the active components of the invention into the aqueous portion of the intestine, (2) better solubility of the peptide in, and transport through, a mucous layer along the intestinal walls. Once the peptide active ingredient reaches the intestinal walls, an uptake enhancer provides better transport through the brush border membrane of the intestine into the blood, via either transcellular or paracellular transport. As discussed in more detail below, many preferred compounds may provide both functions. In those instances, preferred embodiments utilizing both of these functions may do so by adding only one additional compound to the pharmaceutical composition. In other embodiments, separate absorption enhancers may provide the two functions separately.

Each of the preferred ingredients of the pharmaceutical composition of the invention is separately discussed below. Combinations of multiple pH-lowering agents, or multiple enhancers can be used as well as using just a single pH-lowering agent and/or single enhancer. Some preferred combinations are also discussed below.

Peptide Active Ingredients

Peptide active ingredients which may benefit from oral delivery in accordance with the invention include any therapeutic agent that is physiologically active and has a plurality of amino acids and at least one peptide bond in its molecular structure and one site that can be amidated. Amidation of the peptide can be achieved either by chemical or enzymatic means, or by a combination of the two. A preferred method of amidation is by the action of peptidylglycine-amidating monooxygenase.

Preferably, the peptide is extended by a glycine at the C-terminal end when produced by recombinant technology and the C-terminus is amidated by enzymatic reaction. Alternatively, amino acid side chains suitable for amidation can also be amidated by chemical reaction.

Also, preferably, these peptide active ingredients are linked to an MT sequence to facilitate their absorption from the intestine. The MT must be protected from cleavage by proteases in the stomach and intestine before its absorption. However, once absorbed, the MT should be able to be at least partially removed by proteases to free up the active peptide.

The MT can comprise an amino acid sequence, preferably a signal peptide or signal sequence. A "signal peptide," as used herein, is a sequence of amino acids generally but not necessarily of a length of about 10 to about 50 or more amino acid residues, many (typically about 55-60%) residues of which are hydrophobic such that they have a hydrophobic, lipid-soluble portion. The hydrophobic portion is a common, major motif of the signal peptide, and it is often a central part of the signal peptide of proteins secreted from cells. A signal peptide is a sequence of amino acids that facilitates the export of cytoplasmic proteins. The signal peptides of this invention, as discovered herein, are also "importation competent," i.e., capable of penetrating through the cell membrane from outside the cell to the interior of the cell. The amino acid residues can be mutated and/or modified (i.e., to form mimetics) so long as the modifications do not affect the translocation-mediating function of the peptide. Thus the word "peptide" includes mimetics and the word "amino acid" includes modified amino acids, as used herein, unusual amino acids, and D-form amino acids. All importation competent signal peptides encompassed by this invention have the function of mediating translocation across a cell membrane from outside the cell to the interior of the cell. They may also retain their ability to allow the export of a protein from the cell into the external milieu. A putative signal peptide can easily be tested for this importation activity following the teachings provided herein, including testing for specificity for any selected cell type.

The following Table 1 exemplifies amino acid sequences, each of which can be used as an MT.

TABLE 1

Amino Acid Sequences of Some MT Peptides and Their Sources

| SEQUENCE | SEQUENCE DERIVATION | SOURCE |
|---|---|---|
| ALA-ALA-VAL-ALA-LEU-LEU-PRO-ALA-VAL-LEU-LEU-ALA-LEU-LEU-ALA-PRO-VAL-ASN-ARG-LYS-ARG-ASN-LYS-LEU-MET-PRO (SEQ ID No: 3) | Signal Peptide from Kaposi Fibroblast Growth Factor | U.S. Pat. No. 5,807,746 |
| TYR-GLY-ARG-LYS-LYS-ARG-ARG-GLN-ARG-ARG-ARG (SEQ ID No: 4) | Protein Transduction Domain of HIV TAT Protein | Schwarz et al. (1999), Science 285: 1569 |
| VAL-THR-VAL-LEU-ALA-LEU-GLY-ALA-LEU-ALA- | Signal Sequence of | Zhang et al. (1988) PNAS |

TABLE 1-continued

Amino Acid Sequences of Some MT Peptides and Their Sources

| SEQUENCE | SEQUENCE DERIVATION | SOURCE |
|---|---|---|
| GLY-VAL-GLY-VAL-GLY (SEQ ID No: 5) | Human Integrin $\beta_3$ | 95: 9184 |
| 38 kDa Protein | HSV-VP22 Protein | Phelan et al. (1998), Nature Biotechnology 16: 440 |
| ALA-ALA-VAL-LEU-LEU-PRO-VAL-LEU-LEU-ALA-ALA-PRO (SEQ ID No: 6) | Modified from 16-residue hydrophobic region of signal sequence of Kaposi fibroblast growth factor | Rojas et al (1998) Nature Biotechnology 16: 370 |

The MT can also comprise fatty acids and/or bile acids. Such molecules, when used, are linked to the active peptide by an amino acid bridge which is subject to cleavage by proteases in the plasma. Alternatively, the MT can be linked to the active peptide by a non-peptidyl linkage, in which case the in vivo enzyme that cleaves the linkage may be an enzyme other than protease. The amino acid bridge must be a target for cleavage by at least one plasma protease. Plasma proteases as well as their target sequences are well known in the art. Table 2 illustrates some of these enzymes as well as their specific targets

TABLE 2

Plasma Proteases and their Specific Targets

| PROTEASE | SPECIFIC TARGET | REMARKS |
|---|---|---|
| Caspase-1 | Tyr-Val-Ala-Asp-Xaa\* (SEQ ID No: 7) | |
| Caspase-3 | Asp-Xaa-Xaa-Asp-Xaa (SEQ ID No: 8) | |
| Proprotein convertase 1 | Arg-(Xaa)$_n$-Arg-Xaa (SEQ ID No: 9, 20 & 21) | n = 2, 4 or 6 |
| | Lys-(Xaa)$_n$-Arg-Xaa (SEQ ID No: 10, 22 & 23) | n = 2, 4, or 6 |
| | Arg-Arg-Xaa Lys-Arg-Xaa | |
| Proprotein convertase 2 | same as proprotein convertase 1 | |
| Proprotein convertase 4 | Gly-Arg-Thr-Lys-Arg-Xaa (SEQ ID No: 11) | |
| Proprotein convertase 4 PACE 4 | Arg-Val-Arg-Arg-Xaa (SEQ ID No: 12) | |

TABLE 2-continued

Plasma Proteases and their Specific Targets

| PROTEASE | SPECIFIC TARGET | REMARKS |
|---|---|---|
| | Decanoyl-Arg-Val-Arg-Arg-Xaa (SEQ ID No: 13) | |
| Prolyl oligopeptidase | Pro-Xaa | |
| Endothelin cleaving enzyme followed by dipeptidyl-peptidase IV | Trp-Val-Pro-Xaa (SEQ ID No: 14) Trp-Val-Ala-Xaa (SEQ ID No: 15) | |
| Signal peptidase | | depends on nearby amino acid |
| Neprilysin followed by dipeptidyl-peptidase IV | Xaa-Phe-Xaa-Xaa (SEQ ID No: 16) | broad specificity, max length = 40 amino acids |
| | Xaa-Tyr-Xaa-Xaa (SEQ ID No: 17) | |
| | Xaa-Trp-Xaa-Xaa (SEQ ID No: 18) | |
| Renin followed by dipeptidyl-peptidase IV | Asp-Arg-Tyr-Ile-Pro-Phe-His-Leu-Leu-Val-Tyr-Ser (SEQ ID No: 19) | substitute Pro or Ala for Val & Ser |

*The N-terminal side of bolded amino acids is the specific target for the protease cleavage.

The invention, by several mechanisms, suppresses the degradation of the active ingredient by protease that would otherwise tend to cleave one or more of the peptide bonds of the active ingredient.

Both synthetic and natural peptides can be orally delivered in accordance with the invention. Peptide active compounds of the invention include, but are not limited to, insulin, vasopressin, calcitonin (including not only the preferred salmon calcitonin, but other calcitonins as well) and parathyroid hormones and analogs thereof. Other examples include calcitonin gene-related peptide, luteinizing hormone-releasing factor, erythropoietin, tissue plasminogen activators, human growth hormone, adrenocorticototropin, various interleukins, enkephalin, glucagon-like peptide 1, and all analogs thereof. Many others are known in the art. It is expected that any pharmaceutical compound having peptide bonds which would be subject to cleavage in the gastrointestinal tract would benefit from oral delivery in accordance with the present invention because of the enhancement of absorption of such compounds from the intestine coupled with the reduction in such cleavage that is afforded by the present invention.

When salmon calcitonin is used, it preferably comprises from 0.02 to 0.2 percent by weight relative to the total weight of the overall pharmaceutical composition (exclusive of enteric coating) Salmon calcitonin is commercially available (for example, from BACHEM, Torrence, Calif.). Alternatively it may be synthesized by known methods, some of which are discussed briefly below. Other peptide active agents should be present at higher or lower concentrations depending on desired target blood concentrations for the active compound and its bioavailability in the oral delivery system of the invention.

Salmon calcitonin precursors may be made by either chemical or recombinant syntheses known in the art. Precursors of other amidated peptide active agents may be made in like manner. Recombinant production is believed to be significantly more cost effective. Precursors are converted to active salmon calcitonin by amidation reactions that are also known in the art. For example, enzymatic amidation is described in U.S. Pat. No. 4,708,934 and European Patent Publications 0 308 067 and 0 382 403. Recombinant production is preferred for both the precursor and the enzyme that catalyzes the conversion of the precursor to salmon calcitonin. Such recombinant production is discussed in *Biotechnology*, Vol. 11 (1993) pp. 64-70, which further describes a conversion of a precursor to an amidated product. The recombinant product reported there is identical to natural salmon calcitonin, and to salmon calcitonin produced using solution and solid phase chemical peptide synthesis.

When an MT is linked to the active peptide ingredient of the invention, it may be made accomplished by either chemical or recombinant syntheses known in the art. By "linking" as used herein is meant that the biologically active peptide is associated with the MT in such a manner that when the MT crosses the cell membrane, the active peptide is also imported across the cell membrane. Examples of such means of linking include (A) linking the MT to the active peptide by a peptide bond, i.e., the two peptides (the peptide part of the MT and the active peptide) can be synthesized contiguously; (B) linking the MT to the active peptide by a non-peptide covalent bond (such as conjugating a signal peptide to a protein with a crosslinking reagent); (C) chemical ligation methods can be employed to create a covalent bond between the carboxy-terminal amino acid of an MT such as a signal peptide and the active peptide.

Examples of method (A) are shown below wherein a peptide is synthesized, by standard means known in the art, (Merrifield, J. Am. Chem. Soc. 85:2149-2154, 1963; and Lin et al., Biochemistry 27:5640-5645, 1988) and contains, in linear order from the amino-terminal end, a signal peptide sequence (the MT), an amino acid sequence that can be cleaved by a plasma protease, and a biologically active amino acid sequence. Such a peptide could also be produced through recombinant DNA techniques, expressed from a recombinant construct encoding the above-described amino acids to create the peptide. (Sambrook et al., Molecular Cloning: A Laboratory Manual, 2nd Ed., Cold Spring Harbor Laboratory, Cold Spring Harbor, N.Y., 1989).

For method (B), either a peptide bond, as above, can be utilized or a non-peptide covalent bond can be used to link the MT with the biologically active peptide, polypeptide or protein. This non-peptide covalent bond can be formed by methods standard in the art, such as by conjugating the MT to the peptide, polypeptide or protein via a crosslinking reagent, for example, glutaraldehyde. Such methods are standard in the art. (Walter et al., Proc. Natl. Acad. Sci. USA 77:5197; 1980).

For method (C), standard chemical ligation methods, such as using chemical crosslinkers interacting with the carboxy-terminal amino acid of a signal peptide, can be utilized. Such methods are standard in the art (Goodfriend et al., Science 143:1344; 1964, which uses water-soluble carbodiimide as a ligating reagent) and can readily be performed to link the carboxy terminal end of the signal peptide to any selected biologically active molecule.

The production of the preferred recombinant salmon calcitonin (rsCT) may proceed, for example, by producing glycine-extended salmon calcitonin precursor in *E. coli* as a soluble fusion protein with glutathione-S-transferase. The glycine-extended precursor has a molecular structure that is identical to active salmon calcitonin except at the C-terminal (where salmon calcitonin terminates -pro-$NH_2$, while the precursor terminates -pro-gly. An α-amidating enzyme described in the publications above catalyzes conversion of precursors to salmon calcitonin. That enzyme is preferably recombinantly produced, for example, in Chinese Hamster Ovary (CHO) cells) as described in the Biotechnology article cited above. Other precursors to other amidated peptides may be produced in like manner.

Peptides that are not amidated naturally may also be produced in like manner and amidated in a similar fashion according to the invention.

The pH-Lowering Agent and Protease Inhibitor

The total amount of the pH-lowering compound to be administered with each administration of salmon calcitonin should preferably be an amount which, when it is released into the intestine, is sufficient to lower the local intestinal pH substantially below the pH optima for proteases found there. The quantity required will necessarily vary with several factors including the type of pH-lowering agent used (discussed below) and the equivalents of protons provided by a given pH-lowering agent. In practice, the amount required to provide good bioavailability is an amount which, when added to a solution of 10 milliliters of 0.1 M sodium bicarbonate, lowers the pH of that sodium bicarbonate solution to no higher than 5.5, and preferably no higher than 4.7, most preferably no higher than 3.5. Enough acid to lower pH, in the foregoing test, to about 2.8 may be used in some embodiments. Preferably at least 300 milligrams, and more preferably at least 400 milligrams of the pH-lowering agent are used in the pharmaceutical composition of the invention. The foregoing preferences relate to the total combined weight of all pH-lowering agents where two or more of such agents are used in combination. The oral formulation should not include an amount of any base which, when released together with the pH-lowering compound, would prevent the pH of the above-described sodium bicarbonate test from dropping to 5.5 or below.

The pH-lowering agent of the invention may be any pharmaceutically acceptable compound that is not toxic in the gastrointestinal tract and is capable of either delivering hydrogen ions (a traditional acid) or of inducing higher hydrogen ion content from the local environment. It may also be any combination of such compounds. It is preferred that at least one pH-lowering agent used in the invention have a pKa no higher than 4.2, and preferably no higher than 3.0. It is also preferred that the pH lowering agent have a solubility in water of at least 30 grams per 100 milliliters of water at room temperature.

Examples of compounds that induce higher hydrogen ion content include aluminum chloride and zinc chloride. Pharmaceutically acceptable traditional acids include, but are not limited to acid salts of amino acids (e.g., amino acid hydrochlorides) or derivatives thereof. Examples of these are acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine and valine.

Other examples of useful pH-lowering compounds include carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, valeric, and the like.

Other useful pH-lowering agents that might not usually be called "acids" in the art, but which may nonetheless be useful in accordance with the invention are phosphate esters (e.g., fructose 1, 6 diphosphate, glucose 1, 6 diphosphate, phosphoglyceric acid, and diphosphoglyceric acid). CARBOPOL® (Trademark BF Goodrich) and polymers such as polycarbophil may also be used to lower pH.

Any combination of pH lowering agent that achieves the required pH level of no higher than 5.5 in the sodium bicarbonate test discussed above may be used. One preferred embodiment utilizes, as at least one of the pH-lowering agents of the pharmaceutical composition, an acid selected from the group consisting of citric acid, tartaric acid and an acid salt of an amino acid.

When salmon calcitonin is the peptide active agent, certain ratios of pH-lowering agent to salmon calcitonin have proven especially effective. It is preferred that the weight ratio of pH-lowering agent to salmon calcitonin exceed 200:1, preferably 800:1 and most preferably 2000:1.

An alternative or a supplement to the use of pH-lowering agents is the use of protease inhibitors, in particular inhibitors of intestinal proteases. The following Table 3 illustrates some of the known intestinal proteases.

TABLE 3

Intestinal Proteases and their Specific Targets

| PROTEASE | TARGET SITE | pH OPTIMUM | REMARKS |
|---|---|---|---|
| Trypsin | Lys-Xaa | 8 | |
| | Arg-Xaa | | |
| Chymotrypsin | Tyr-Xaa | 7.0-9.0 | |
| | Phe-Xaa | | |
| | Trp-Xaa | | |
| Elastase | Ala-Xaa | 8.8 | |
| | Val-Xaa | | |
| | Leu-Xaa | | |
| | Ile-Xaa | | |
| | Gly-Xaa | | |
| | Ser-Xaa | | |
| Kallikrein | Arg-Xaa | 7.0-8.0 | |
| | Phe-Arg-Xaa | | preferred |
| | Leu-Arg-Xaa | | preferred |
| Carboxypeptidase | Xaa-Xaa | 7.0-9.0 | from C-terminal |

Optional Ingredients—The Absorption Enhancer

When used, the absorption enhancers are preferably present in a quantity that constitutes from 0.1 to 20.0 percent by weight, relative to the overall weight of the pharmaceutical composition (exclusive of the enteric coating). Preferred absorption enhancers are surface active agents which act both as solubility enhancers and uptake enhancers. Generically speaking, "solubility enhancers" improve the ability of the components of the invention to be solubilized in either the aqueous environment into which they are originally released or into the lipophilic environment of the mucous layer lining the intestinal walls, or both. "Transport (uptake) enhancers" (which are frequently the same surface active agents used as solubility enhancers) are those which facilitate the ease by which peptide agents cross the intestinal wall.

One or more absorption enhancers may perform one function only (e.g., solubility), or one or more absorption enhancers may perform the other function only (e.g., uptake), within the scope of the invention. It is also possible to have a mixture of several compounds some of which provide improved solubility, some of which provide improved uptake and/or some of which perform both. Without intending to be bound by theory, it is believed that uptake enhancers may act by (1) increasing disorder of the hydrophobic region of the membrane exterior of intestinal cells, allowing for increased transcellular transport; or (2) leaching membrane proteins resulting in increased transcellular transport; or (3) widening pore radius between cells for increased paracellular transport.

Surface active agents are believed to be useful both as solubility enhancers and as uptake enhancers. For example, detergents are useful in (1) solubilizing all of the active components quickly into the aqueous environment where they are originally released, (2) enhancing lipophilicity of the components of the invention, especially the peptide active agent, aiding its passage into and through the intestinal mucus, (3) enhancing the ability of the normally polar peptide active agent to cross the epithelial barrier of the brush border membrane; and (4) increasing transcellular or paracellular transport as described above.

When surface active agents are used as the absorption enhancers, it is preferred that they be free flowing powders for facilitating the mixing and loading of capsules during the manufacturing process. Because of inherent characteristics of salmon calcitonin and other peptides (e.g., their isoelectric point, molecular weight, amino acid composition, etc.) certain surface active agents interact best with certain peptides. Indeed, some can undesirably interact with the charged portions of salmon calcitonin and prevent its absorption, thus undesirably resulting in decreased bioavailability. It is preferred, when trying to increase the bioavailability of salmon calcitonin or other peptides that any surface active agent used as an absorption enhancer be selected from the group consisting of (i) anionic surface active agents that are cholesterol derivatives (e.g., bile acids), (ii) cationic surface agents (e.g., acyl carnitines, phospholipids and the like), (iii) non-ionic surface active agents, and (iv) mixtures of anionic surface active agents (especially those having linear hydrocarbon regions) together with negative charge neutralizers. Negative charge neutralizers include but are not limited to acyl carnitines, cetyl pyridinium chloride, and the like. It is also preferred that the absorption enhancer be soluble at acid pH, particularly in the 3.0 to 5.0 range.

One especially preferred combination that has worked well with salmon calcitonin mixes cationic surface active agents with anionic surface active agents that are cholesterol derivatives, both of which are soluble at acid pH.

A particularly preferred combination is an acid soluble bile acid together with a cationic surface active agent. An acyl carnitine and sucrose ester is a good combination. When a particular absorption enhancer is used alone, it is preferred that it be a cationic surface active agent. Acyl carnitines (e.g., lauroyl carnitine), phospholipids and bile acids are particularly good absorption enhancers, especially acyl carnitine. Anionic surfactants that are cholesterol derivatives are also used in some embodiments. It is the intent of these preferences to avoid interactions with the peptide agent that interfere with absorption of peptide agent into the blood.

To reduce the likelihood of side effects, preferred detergents, when used as the absorption enhancers of the invention, are either biodegradable or reabsorbable (e.g., biologically recyclable compounds such as bile acids, phospholipids, and/or acyl carnitines), preferably biodegradable. Acylcarnitines are believed particularly useful in enhancing paracellular transport. When a bile acid (or another anionic detergent lacking linear hydrocarbons) is used in combination with a cationic detergent, salmon calcitonin is better transported both to and through the intestinal wall.

Preferred absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g., Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g., Igepal CO series), polyoxyethylene sorbitan esters (e.g., Tween-20, Tween-80 etc.); (d) anionic surfactants such as dioctyl sodium sulfosuccinate; (e) lyso-phospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids; (h) medium-chain glycerides which are mixtures of mono-, di- and triglycerides containing medium-chain-length fatty acids (caprylic, capric and lauric acids); (i) ethylene-diaminetetraacetic acid; (j) cationic surfactants such as cetylpyridinium chloride; (k) fatty acid derivatives of polyethylene glycol such as Labrasol, Labrafac, etc.; and (l) alkylsaccharides such as lauryl maltoside, lauroyl sucrose, myristoyl sucrose, palmitoyl sucrose, etc.

In some preferred embodiments, and without intending to be bound by theory, cationic ion exchange agents (e.g., detergents) are included to provide solubility enhancement by another possible mechanism. In particular, they may prevent the binding of salmon calcitonin or other peptide active agents to mucus. Preferred cationic ion exchange agents include protamine chloride or any other polycation.

Other Optional Ingredients

It is preferred that a water-soluble barrier separate the protease inhibitors and/or the pH-lowering agent from the acid resistant protective vehicle. A conventional pharmaceutical capsule can be used for the purpose of providing this barrier. Many water soluble barriers are known in the art and include, but are not limited to, hydroxypropyl methylcellulose and conventional pharmaceutical gelatins.

In some preferred embodiments, another peptide (such as albumin, casein, soy protein, other animal or vegetable proteins and the like) is included to reduce non-specific adsorption (e.g., binding of peptide to the intestinal mucus barrier) thereby lowering the necessary concentration of the expensive peptide active agent. When added, the peptide is preferably from 1.0 to 10.0 percent by weight relative to the weight of the overall pharmaceutical composition (excluding protective vehicle). Preferably, this second peptide is not physiologically active and is most preferably a food peptide such as soy bean peptide or the like. Without intending to be bound by theory, this second peptide may also increase bioavailability by acting as a protease scavenger that desirably competes with the peptide active agent for protease interaction. The second peptide may also aid the active compound's passage through the liver.

All pharmaceutical compositions of the invention may optionally also include common pharmaceutical diluents, glidents, lubricants, gelatin capsules, preservatives, colorants and the like in their usual known sizes and amounts.

The Protective Vehicle

Any carrier or vehicle that protects the peptide agent from stomach proteases and then dissolves so that the other ingredients of the invention may be released in the intestine is suitable. Many such enteric coatings are known in the art, and are useful in accordance with the invention. Examples include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, the active peptide, absorption enhancers such as solubility and/or uptake enhancer(s), and pH-lowering compound(s), are included in a sufficiently viscous protective syrup to permit protected passage of the components of the invention through the stomach.

Suitable enteric coatings for protecting the peptide agent from stomach proteases may be applied, for example, to capsules after the remaining components of the invention have been loaded within the capsule. In other embodiments, enteric coating is coated on the outside of a tablet or coated on the outer surface of particles of active components which are then pressed into tablet form, or loaded into a capsule, which is itself preferably coated with an enteric coating.

It is very desirable that all components of the invention be released from the carrier or vehicle, and solubilized in the intestinal environment as simultaneously as possible. It is preferred that the vehicle or carrier release the active components in the small intestine where uptake enhancers that increase transcellular or paracellular transport are less likely to cause undesirable side effects than if the same uptake enhancers were later released in the colon. It is emphasized, however, that the present invention is believed effective in the colon as well as in the small intestine. Numerous vehicles or carriers, in addition to the ones discussed above, are known in the art. It is desirable (especially in optimizing how simultaneously the components of the invention are released) to keep the amount of enteric coating low. Preferably, the enteric coating adds no more than 30% to the weight of the remainder of pharmaceutical composition (the "remainder" being the pharmaceutical composition exclusive of enteric coating itself). More preferably, it adds less than 20%, especially from 12% to 20% to the weight of the uncoated composition. The enteric coating preferably should be sufficient to prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute.

Other Preferences

It is preferred that the weight ratio of pH-lowering agent(s) and/or protease inhibitors to absorption enhancer(s), when present, be between 3:1 and 20:1, preferably 4:1-12:1, and most preferably 5:1-10:1. The total weight of all pH-lowering agents and/or protease inhibitors and the total weight of all absorption enhancers in a given pharmaceutical composition is included in the foregoing preferred ratios. For example, if a pharmaceutical composition includes two pH-lowering agents and three absorption enhancers, the foregoing ratios will be computed on the total combined weight of both pH-lowering agents and the total combined weight of all three absorption enhancers.

It is preferred that the pH-lowering agent and/or protease inhibitor, the peptide active agent and the absorption enhancer, when present, (whether single compounds or a plurality of compounds in each category) be uniformly dispersed in the pharmaceutical composition. In one embodiment, the pharmaceutical composition comprises granules that include a pharmaceutical binder having the peptide active agent, the pH-lowering agent and the absorption enhancer uniformly dispersed within said binder. Preferred granules may also consist of an acid core, surrounded by a uniform layer of organic acid, a layer of enhancer and a layer of peptide that is surrounded by an outer layer of organic acid. Granules may be prepared from an aqueous mixture consisting of pharmaceutical binders such as polyvinyl pyrrolidone or hydroxypropyl methylcellulose, together with the pH-lowering agents, absorption enhancers and peptide active agents of the invention.

Manufacturing Process

A preferred pharmaceutical composition of the invention includes a size OO gelatin capsule filled with 0.25 mg. of salmon calcitonin linked to an MT, 400 mg. of granular citric acid (available for example from Archer Daniels Midland Corp.), 50 mg. of taurodeoxycholic acid (available for example from SIGMA), 50 mg. lauroyl carnitine (SIGMA).

All of the ingredients are preferably for eventual insertion into the gelatin capsule, and are preferably powders which may be added to a blender in any order. Thereafter, the blender is run for about three minutes until the powders are thoroughly intermixed. Then the mixed powders are loaded into the large end of the gelatine capsules. The other end of the capsule is then added, and the capsule snapped shut. 500 or more such capsules may be added to a coating device (e.g., Vector LDCS 20/30 Laboratory Development Coating System (available from Vector Corp., Marion, Iowa)).

An enteric coating solution is made as follows. Weigh 500 grams of EUDRAGIT L30 D-55 (a methacrylic acid copolymer with methacylic acid methyl ester, an enteric coating available from RÖHM Tech Inc., Maidan, Mass.). Add 411 grams distilled water, 15 grams triethyl citrate and 38 grams talc. This amount of coating will be sufficient to coat about 500 size OO capsules.

The capsules are weighed and placed into the drum of the coating machine. The machine is turned on to rotate the drum (now containing capsules) at 24-28 rpm. The temperature of inlet sprayer is preferably about 45° C. Exhaust temperatures are preferably about 30° C. Uncoated capsule temperature is preferably about 25° C. Air flow is about 38 cubic feet per minute.

A tube from the machine is then inserted into the coating solution prepared as discussed above. The pump is then turned on for feeding solution into the coating device. Coating then proceeds automatically. The machine can be stopped at any time to weigh capsules to determine if the coating amount is sufficient. Usually coating is allowed to proceed for 60 minutes. The pump is then turned off for about five minutes while the machine is still running to help dry the coated capsules. The machine can then be turned off. The capsule coating is then complete, although it is recommended that the capsules be air dried for about two days.

Because of the enhanced bioavailability provided by the present invention, the concentration of expensive salmon calcitonin in the pharmaceutical preparation of the invention may be kept relatively low. Specific formulation examples are set forth in examples infra.

Treatment of Patients

When salmon calcitonin is chosen as active ingredient for treatment of osteoporosis, periodic administration is recommended. Salmon calcitonin is metabolized quickly with a half-life of only 20-40 minutes following subcutaneous administration in man. However, its beneficial effect on osteoclasts is much longer lasting, and may last for more than 24 hours notwithstanding rapid decrease in blood levels. There is usually no detectable blood levels more than two hours after injection of salmon calcitonin at conventional dosages. Accordingly, periodic administration of one dose about 5 days per week is preferred. Subcutaneous administration of salmon calcitonin (100 International units) has frequently resulted in peak serum concentration of about 250 picograms per milliliter. Nasally administered salmon calcitonin (200 International units) has proven effective against osteoporosis at peak levels as low as 10 picograms per milliliter. Some patients report some gastrointestinal distress at high peak levels (e.g., at or above 200 picograms per milliliter). Accordingly, it is preferred that serum salmon calcitonin peak between 10 and 150 picograms per milliliter, more preferably between 10 and 50 picograms per milliliter. The serum levels may be measured by radioimmunoassay techniques known in the art. The attending physician may monitor patient response, salmon calcitonin blood levels, or surrogate markers of bone disease (such as urinary pyridinoline or deoxypyridinoline), especially during the initial phase of treatment (1-6 months). He may then alter the dosage somewhat to account for individual patient metabolism and response.

It is preferred that a single capsule be used at each administration because a single capsule best provides simultaneous release of the polypeptide, pH-lowering agent and absorption enhancers. This is highly desirable because the acid is best able to reduce undesirable proteolytic attack on the polypeptide when the acid is released in close time proximity to release of the polypeptide. Near simultaneous release is best achieved by administering all components of the invention as a single pill or capsule. However, the invention also includes, for example, dividing the required amount of acid and enhancers, when used, among two or more capsules which may be administered together such that they together provide the necessary amount of all ingredients. "Pharmaceutical composition," as used herein includes a complete dosage appropriate to a particular administration to a human patient regardless of how it is subdivided so long as it is for substantially simultaneous administration.

Example 1

Effect of Carboxy Terminal Amidation on the Oral Bioavailability of Salmon Calcitonin (sCT)

A study was carried out in a dog model to compare the pharmacokinetic parameters of orally delivered glycine-extended sCT (sCTgly) with those of amidated sCT (sCT-$NH_2$).

Eight adult male Beagle dogs, weighing between 12 and 16 kg, were used in this study. Dogs were fasted overnight prior to administration of the test peptide, but were allowed free access to water. A wash-out period of at least 1 week occurred between experiments for each dog. Each dog received an orally administered, enteric coated gelatin capsule that contained 1.11 mg of sCTgly in week 1 and 1.11 mg of sCT-$NH_2$ in week 2. The total composition of each capsule is shown in Table 4. Prior to capsule administration, a 20-gauge intravenous (IV) catheter was inserted into a brachial vein for the collection of blood samples. Two pre-dose samples of 3 ml each were collected from the brachial vein.

TABLE 4

The Composition of sCT-gly and sCTNH$_2$ Capsules

| Capsule | Granular Citric Acid (mg) | LLC (mg) | sCT-gly (mg) | sCT-NH$_2$ (mg) | Talc (mg) |
|---|---|---|---|---|---|
| sCT-gly capsule | 596 | 62 | 1.11 | | 30 |
| sCTNH$_2$ capsule | 576 | 58 | | 1.11 | 29 |

After administration of the capsule, 3 ml blood samples were collected from the brachial vein at 15 minute intervals up to 240 minutes post-administration. Blood samples were collected into new heparinized Monovette sampling syringes. Samples were placed on ice before being centrifuged for 10 minutes at approximately 2750 rpm at 2-8° C. The plasma supernatant was transferred to color-coded microcentrifuge tubes labeled with the time point and stored frozen at −20° C. prior to analysis to determine the concentration of sCTgly or sCT-$NH_2$.

The concentration of sCTgly in plasma was determined by radioimmunoassay with an RIA kit from Peninsula Laboratories. sCT-$NH_2$ concentration in plasma was determined by a sandwich ELISA immunoassay using a kit from Diagnostic Systems Laboratories Inc. From the pharmacokinetic profile of sCTgly or sCT-$NH_2$ in plasma, the parameters of Cmax (peak of plasma concentration in pg/ml) and AUC (Area under the Curve) were determined. All measured values were normalized for a 1 mg peptide dose for either of the two peptides. The mean for each of these parameters is shown in Table 5.

TABLE 5

| Peptide | Mean Cmax* ± SEM (pg/ml) | Mean AUC* ± SERM (pg · min/ml) |
|---|---|---|
| sCTgly | 485 ± 106 | 25,125 ± 5,525 |
| SCT-NH$_2$ | 3,199 ± 602 | 148,000 ± 18,200 |

*Adjusted to a 1 mg dose

The mean Cmax of sCT with a C-terminal amide is 6.6 times greater than that of sCTgly. The mean AUC, which is an indirect measure of bioavailability, is 5.9 times greater for sCT-$NH_2$ than for sCTgly. Thus, for these two peptides, which are identical except for the presence of a glycine or an amide group at the C-terminus, there is a dramatic difference in the amount of peptide measured in plasma after oral delivery, and this can be directly attributed to the presence of the C-terminal amide group.

Example 2

Comparison of the Bioavailability of Amidated and Non-Amidated Analogs of Parathyroid Hormone (PTH)

Two separate studies were carried out in a dog model to determine the pharmacokinetic parameters of orally delivered PTH analogs. The analog used in the first study was PTH1-34-OH. In the second study, a slightly smaller analog, PTH1-31$NH_2$, was used. Apart from the small difference in size (three amino acids), the main difference between the two molecules is that the 1-34 peptide has a free acid at the C-terminus and the 1-31 peptide has an amidated C-terminus.

Eight adult male Beagle dogs, weighing between 12 and 16 kg, were used in the study for PTH1-34-OH. In the PTH1-31$NH_2$ study, six of these same dogs were used. Dogs were fasted overnight prior to administration of the test peptide, but were allowed free access to water. A wash-out period of at least 1 week occurred between experiments for each dog. Each dog received an orally administered, enteric coated gelatin capsule that contained 2.64 mg of PTH1-34-OH in the first study and 2.38 mg of PTH1-31$NH_2$ in the second study. The total composition of each capsule is shown in Table 6. Prior to capsule administration, a 20-gauge intravenous (IV) catheter was inserted into a brachial vein for the collection of blood samples. Two pre-dose samples of 3 ml each were collected from the brachial vein.

TABLE 6

The Composition of PTH1-34-OH and PTH1-31NH$_2$ Capsules

| Capsule | Granular Citric Acid (mg) | LLC (mg) | PTH1-34-OH (mg) | PTH1-31NH$_2$ (mg) | Talc (mg) |
|---|---|---|---|---|---|
| PTH1-34-OH Capsule | 472 | 47 | 2.64 | | 24 |
| PTH1-31NH$_2$ Capsule | 576 | 58 | | 2.38 | 29 |

After administration of the capsule, 3 mL blood samples were collected from the brachial vein at 15 minute intervals up to 240 minutes post-administration. Blood samples were collected into new heparinized Monovette sampling syringes. The samples were placed on ice before being centrifuged for 10 minutes at approximately 2750 rpm at 2-8° C. The plasma supernatant was transferred to color-coded microcentrifuge tubes labeled with the time point and stored frozen at −20° C. prior to analysis of the concentration of PTH1-34-OH or PTH1-31NH$_2$.

The concentration of PTH1-34-OH in plasma was determined using a RIA kit from Penninsula Laboratories. PTH1-31NH$_2$ was quantified using a competitive ELISA developed at Unigene Laboratories. From the pharmacokinetic profile of PTH1-34-OH or PTH1-31NH$_2$ in plasma, the parameters of Cmax (peak of plasma concentration in pg/ml) and AUC (Area under the Curve) were calculated. The mean values for each of these parameters is shown in Table 7.

TABLE 7

| Peptide | Mean Cmax* ± SEM (pg/ml) | Mean AUC* ± SEM (pg · min/ml) |
|---|---|---|
| PTH1-34-OH | 314 ± 117 | 11,893 ± 3,366 |
| PTH1-31NH$_2$ | 2,155 ± 456 | 116,400 ± 32,100 |

*Adjusted to a 1 mg dose

The mean Cmax of PTH1-31NH$_2$ is approximately 6.25 times greater than that of PTH1-34-OH, and the mean AUC, an indirect measure of bioavailability, is 9.8 times greater for PTH1-31NH$_2$. Although the PTH1-31NH$_2$ molecule is smaller by 3 amino acids than PTH1-34-OH, this small difference in molecular weight between the two peptides (3718 Daltons and 4118 Daltons respectively) does not account for the difference seen in bioavailabilities. Therefore, the important difference between the two peptides is the presence or absence of the C-terminal amide group.

Example 3

Comparison of the Bioavailability of an Analog of Parathyroid Hormone, PTH1-34, with or without a C-terminal Amide Group, by Intraduodenal Administration in Rats Female Sprague-Dawley rats (250-275 g) (n=6 for PTH1-34-OH and n=7 for PTH1-34NH$_2$) were anesthetized with ketamine and xylazine prior to the insertion of a cannula in the carotid artery. The cannula was fitted to a three way valve through which blood was sampled and replaced with physiological saline. A midline incision was made in the abdominal cavity and 0.5 ml of formulation was injected directly into the exposed duodenum. The formulation for each peptide contained citric acid (0.5 M), lauroylcarnitine (10 mg/ml), salmon calcitonin (included as an internal marker) (0.5 mg/ml) and either PTH1-34-OH or PTH1-34NH$_2$ (0.5 mg/ml). Blood (0.5 ml) was collected before and at 5, 15, 30, 60 and 120 minutes after the administration of the formulations. Samples of blood were centrifuged for 10 minutes at 2600×g, and the resulting plasma supernatant was stored at −20° C. The concentration of the peptides in plasma was determined by a competitive enzyme linked immunoassay (ELISA). The absolute bioavailability (i.e., relative to an intravenous dose for each peptide) was calculated from the areas under the curve obtained from plots of the plasma concentration of PTH1-34-OH or PTH1-34NH$_2$ as a function of time.

PTH1-34-OH and PTH1-34NH$_2$ were rapidly absorbed from the rat duodenum within 5 minutes after their administration. The maximum concentration of PTH 1-34-OH was 3.05 ng/ml and that of PTH1-34NH$_2$ was 26.7 ng/ml, which was nearly 9 times greater than the free acid form of PTH (1-34). After 60 minutes, the concentration of PTH1-34NH$_2$ was still nearly 9 times greater than that of PTH1-34-OH (Table 8). The absolute bioavailability of PTH1-34NH$_2$ was 3.68% and that of PTH1-34-OH was 0.45%. These results suggest that the substitution of the amide group at the C-terminus for the OH group improved the maximum peptide concentration in plasma by 8.75 fold and the absolute bioavailability of PTH1-34 by 8.2 fold.

TABLE 8

Effect of C-Terminal Amide on the Pharmacokinetic Profile of PTH1-34

| Time (Min) | PTH1-34-OH ng/ml ± standard error | PTH1-34NH$_2$ ng/ml ± standard error |
|---|---|---|
| 0 | 0.00 | 0.00 |
| 5 | 2.69 ± 1.35 | 26.70 ± 7.84 |
| 15 | 3.05 ± 1.31 | 21.03 ± 4.07 |
| 30 | 1.90 ± 0.81 | 13.13 ± 3.36 |
| 60 | 0.62 ± 0.38 | 5.39 ± 3.08 |
| 120 | 0.81 ± 0.35 | 1.18 ± 1.08 |
| Absolute Bioavailability (%) | 0.45 ± 0.18 | 3.68 ± 0.76 |

Example 4

Effect of C-terminal Amide on the Intraduodenal Absorption of LHRH in Rats

The effect of C-terminal amidation on the absorption of luteinizing hormone-releasing hormone (LHRH-NH$_2$) from the duodenum of anesthetized rats was examined. In this study the absorption characteristics of LHRH-NH$_2$, a naturally occurring C-terminal amidated decapeptide were compared with that of LHRH-COOH, a decapeptide with the same amino acid sequence as that of LHRH-NH$_2$ except that the C-terminal amino acid of LHRH-COOH is gly-COOH instead of gly-NH$_2$. Twelve female rats were anesthetized and implanted with a cannula in the carotid artery for taking blood samples at various times. Six rats were injected in the duodenum through a 27 gauge needle with 0.5 mL of LHRH-NH$_2$ (5 mg/mL) in 0.5M citric acid and lauroylcarnitine (10 mg/mL) and six rats with injected in the duodenum with 0.5 mL LHRH-COOH) (5 mg/mL) in the same formulation. Samples of blood were taken prior to the administration of formulated LHRH-NH$_2$ or LHRH-COOH and at 5, 15, 30, 60, and 120 minutes after peptide administration. The resulting plasma samples were analyzed for LHRH-NH$_2$ or LHRH-COOH by high performance liquid chromatography equipped with a fluorescence detector to measure the concentration of peptide in plasma. The maximum concentration (Cmax) of amidated and non-amidated LHRH was detected in plasma five minutes after peptide administration. Although equal amounts of both forms of LHRH were administered to rats, 5 times as much amidated LHRH, LHRH-NH$_2$, was detected in plasma at five minutes than the free acid form, LHRH-COOH (Table 9). The area under the curve (AUC), a measure of the extent of peptide absorption and bioavailability, was 6 times greater for amdidated LHRH than the free acid form of LHRH (Table 9). These results indicate that amidated peptides in a formulation containing an acid and an enhancer have greater bioavailability than non-amidated peptides.

TABLE 9

Effect of C-terminal amide on the Intraduodenal Absorption of LHRH in Rats

| min | LHRH-NH$_2$ | LHRH-COOH |
|---|---|---|
| 0 | ng/mL ± sem | ng/mL ± sem |
| 5 | 0 | 0 |
| 15 | 3276 ± 893 | 654 ± 103 |
| 30 | 2897 ± 612 | 391 ± 81 |
| 60 | 1282 ± 282 | 163 ± 68 |
| 120 | 382 ± 103 | 56 ± 19 |
| Cmax | 3276 ± 893 | 654 ± 103 |
| AUC | 109350 ± 23652 | 17731 ± 4002 |

Although the present invention has been described in relation to particular embodiments thereof, many other variations and modifications and other uses will become apparent to those skilled in the art. The present invention therefore is not limited by the specific disclosure herein, but only by the claims.

What is claimed is:

1. An oral pharmaceutical composition comprising an active peptide agent that has an amide group at its C-terminus, and is not found in nature with an amide group at its C-terminus, wherein said active peptide agent is a human parathyroid hormone analog having the first 34 amino acids of human parathyroid hormone wherein the 34$^{th}$ amino acid is amidated at its C-terminus, said composition further comprising an absorption enhancer effective to promote bioavailability of said active peptide agent, or a pharmaceutically acceptable pH-lowering agent that is present in said pharmaceutical composition in a quantity which, if said composition were added to ten milliliters of 0.1M aqueous sodium bicarbonate solution, would be sufficient to lower the pH of said solution to no higher than 5.5.

2. The pharmaceutical composition of claim 1 comprising at least one pharmaceutically acceptable pH-lowering agent.

3. The pharmaceutical composition of claim 2 further comprising an acid resistant protective vehicle effective to transport said pharmaceutical composition through the stomach of a patient while preventing contact between said active peptide agent and stomach proteases.

4. The pharmaceutical composition of claim 1, wherein said active peptide agent is prepared by converting a glycine-extended precursor to said active peptide agent.

5. The pharmaceutical composition of claim 1, wherein said active peptide agent comprises an amino acid that contains an amidated side chain.

6. The pharmaceutical composition of claim 2, wherein said pH-lowering agent is present in a quantity which, if said composition were added to ten milliliters of 0.1M aqueous sodium bicarbonate solution, would be sufficient to lower the pH of said solution to no higher than 3.5.

7. The pharmaceutical composition of claim 1, wherein said active peptide agent is linked to a membrane translocator which is capable of being at least partially cleaved in vivo by an enzyme.

8. The pharmaceutical composition of claim 3, wherein said protective vehicle is present at a weight which is no more than 30% of the weight of the remainder of said pharmaceutical composition.

9. The pharmaceutical composition of claim 3, wherein said protective vehicle is present at a weight which is no more than 20% of the weight of the remainder of said pharmaceutical composition.

10. The pharmaceutical composition of claim 3, wherein said protective vehicle is present at a weight which is between 10% and 20% of the weight of the remainder of said pharmaceutical composition.

11. The pharmaceutical composition of claim 3, wherein said protective vehicle is sufficient to prevent breakdown of said pharmaceutical composition in 0.1N HCl for at least two hours, yet permits complete release of all contents of said pharmaceutical composition within 45 minutes after pH is increased to 6.3 in a dissolution bath in which said composition is rotating at 100 revolutions per minute.

12. The pharmaceutical composition of claim 1, comprising an absorption enhancer, wherein the absorption enhancer is a surface active agent.

13. The pharmaceutical composition of claim 12, wherein said surface active agent is absorbable or biodegradable.

14. The pharmaceutical composition of claim 12, wherein said surface active agent is selected from the group consisting of acylcarnitines, phospholipids and bile acids.

15. The pharmaceutical composition of claim 14, wherein said surface active agent is an acylcarnitine.

16. The pharmaceutical composition of claim 15, further including a sucrose ester.

17. The pharmaceutical composition of claim 1, comprising an absorption enhancer, wherein the absorption enhancer is a surface active agent selected from the group consisting of (i) an anionic agent that is a cholesterol derivative, (ii) a mixture of a negative charge neutralizer and an anionic surface active agent, (iii) non-ionic surface active agents, and (iv) cationic surface active agents.

18. The pharmaceutical composition of claim 1, comprising an absorption enhancer is selected from the group consisting of a cationic surfactant and an anionic surfactant that is a cholesterol derivative.

19. The pharmaceutical composition of claim 1, wherein said pharmaceutical composition includes at least two absorption enhancers, one of which is a cationic surface active agent, and another of which is an anionic surface active agent that is a cholesterol derivative.

20. The pharmaceutical composition of claim 19, wherein said anionic surface active agent is an acid-soluble bile acid.

21. The pharmaceutical composition of claim 1, further comprising an amount of a second peptide that is not physiologically active effective to enhance bioavailability of said peptide active agent.

22. The pharmaceutical composition of claim 3, further comprising a water soluble barrier that separates said pH-lowering agent from said protective vehicle.

23. The pharmaceutical composition of claim 2, wherein said composition includes at least one pH-lowering agent that has a pKa no higher than 4.2.

24. The pharmaceutical composition of claim 2, wherein at least one pH-lowering agent has a solubility in water of at least 30 grams per 100 milliliters of water at room temperature.

25. The pharmaceutical composition of claim 3, wherein all ingredients other than said protective vehicle are uniformly dispersed.

26. The pharmaceutical composition of claim 25, wherein said pharmaceutical composition comprises granules containing a pharmaceutical binder and, uniformly dispersed in said binder, said pH-lowering agent, said absorption enhancer and said peptide active agent.

27. The pharmaceutical composition of claim 1, comprising a pharmaceutically acceptable pH-lowering agent and an absorption enhancer wherein said composition is a solid dosage form wherein a weight ratio of said pH-lowering agent to said absorption enhancer is between 3:1 and 20:1.

28. The pharmaceutical composition of claim 1, comprising a pharmaceutically acceptable pH-lowering agent and an absorption enhancer wherein said composition is a solid dosage form wherein the weight ratio of said pH-lowering agent to said absorption enhancer is between 5:1 and 10:1.

29. The pharmaceutical composition of claim 2, wherein said pH-lowering agent is selected from the group consisting of citric acid, tartaric acid and an acid salt of an amino acid.

30. The pharmaceutical composition of claim 2, wherein said pH-lowering agent is present in an amount not less than 300 milligrams.

31. The pharmaceutical composition of claim 30, wherein said pH-lowering agent is present in an amount which is not less than 400 milligrams.

32. The pharmaceutical composition of claim 3, wherein said protective vehicle is a viscous protective syrup.

33. The pharmaceutical composition of claim 3, wherein a water soluble barrier separates said pH-lowering agent from said protective vehicle.

34. A method for modifying a physiologically active peptide to increase its oral bioavailability, while substantially maintaining its physiological activity, said method comprising:
(A) amidating a physiologically active peptide that is not naturally amidated at its C-terminus at said C-terminus, wherein said amidated peptide is human parathyroid hormone analog PTH1-34-NH$_2$; and
(B) orally administering said amidated peptide in combination with (i) at least one absorption enhancer effective to promote bioavailability of said amidated peptide, or (ii) a pH-lowering agent that is present in a pharmaceutical composition comprising said amidated peptide in a quantity which, if said composition were added to ten milliliters of 0.1M aqueous sodium bicarbonate solution, would be sufficient to lower the pH of said solution to no higher than 5.5.

35. The method of claim 34 comprising an absorption enhancer, wherein said amidated peptide and said absorption enhancer are selectively released together with at least one pH-lowering agent and/or protease inhibitor into a patient's intestine following passage of said peptide active agent, absorption enhancer, pH-lowering agent and/or protease inhibitor through said patient's mouth and stomach under protection of an acid resistant protective vehicle which substantially prevents contact between stomach proteases and said peptide agent.

36. The method of claim 34, wherein said amidated peptide is prepared by converting a glycine-extended precursor to said amidated peptide.

37. The method of claim 34, wherein said amidated peptide further includes an amidated side chain.

38. The method of claim 34, wherein said pH-lowering agent and said absorption enhancer are both present.

39. The method of claim 34 comprising a pH-lowering agent, wherein said pH-lowering agent is present in a quantity which, if said composition were added to ten milliliters of 0.1 M aqueous sodium bicarbonate solution, would be sufficient to lower the pH of said solution to no higher than 3.5.

40. The method of claim 35, wherein said protease inhibitor is a stomach and/or intestine protease inhibitor.

41. The method of claim 35, wherein said protease inhibitor inhibits an enzyme selected from the group consisting of pepsin, trypsin, chymotrypsin, elastase, kallikrein and carboxypeptidase.

42. The method of claim 34, wherein said increase in oral bioavailability is the result of enhanced intestinal absorption of the amidated peptide.

\* \* \* \* \*